US011511042B2

(12) United States Patent
Yigal et al.

(10) Patent No.: US 11,511,042 B2
(45) Date of Patent: Nov. 29, 2022

(54) INJECTOR POWER-UP MECHANISM

(71) Applicant: West Pharma. Services IL, Ltd., Ra'anana (IL)

(72) Inventors: Gil Yigal, Gan Yavne (IL); Yossi Bar-El, Beit Arye (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 313 days.

(21) Appl. No.: 16/636,183

(22) PCT Filed: Aug. 7, 2018

(86) PCT No.: PCT/US2018/045506
§ 371 (c)(1),
(2) Date: Feb. 3, 2020

(87) PCT Pub. No.: WO2019/032512
PCT Pub. Date: Feb. 14, 2019

(65) Prior Publication Data
US 2020/0368449 A1    Nov. 26, 2020

Related U.S. Application Data

(60) Provisional application No. 62/543,641, filed on Aug. 10, 2017.

(51) Int. Cl.
*A61M 5/24*    (2006.01)
*A61M 5/315*    (2006.01)
(Continued)

(52) U.S. Cl.
CPC .......... *A61M 5/24* (2013.01); *A61M 5/14248* (2013.01); *A61M 5/14566* (2013.01);
(Continued)

(58) Field of Classification Search
CPC .. A61M 2005/2414; A61M 2005/2496; A61M 5/14566
See application file for complete search history.

(56) References Cited

U.S. PATENT DOCUMENTS 6,336,729 B1    1/2002   Pavelle et al.
7,794,426 B2    9/2010   Briones et al.
(Continued)

FOREIGN PATENT DOCUMENTS

CN    1376524 A    10/2002
EP    2244765 B1   11/2010
(Continued)

OTHER PUBLICATIONS

Int'l Search Report and Written Opinion dated Oct. 26, 2018 in Int'l Application No. PCT/US2018/045506.
(Continued)

*Primary Examiner* — Jenna Zhang
(74) *Attorney, Agent, or Firm* — Blank Rome LLP

(57) ABSTRACT

An injector has a cartridge door movable between a fully closed position and a fully open position. A power supply is employed to power at least one power-operated component of the injector. A power supply circuit electrically connects the power supply with the at least one power-operated component. An electrically insulated arm is movable from a first state, in which the electrically insulated arm electrically disconnects the power supply from the circuit, to a second state, in which the electrically insulated arm connects the power supply with the circuit to provide power to the at least one power-operated component. The insulated arm is coupled to the cartridge door and initially positioned in the first state thereof in the fully closed position of the cartridge door, whereby movement of the cartridge door out of the
(Continued)

fully closed position toward the fully open position moves the arm to the second state thereof.

20 Claims, 9 Drawing Sheets

(51) Int. Cl.
*A61M 5/145* (2006.01)
*A61M 5/142* (2006.01)

(52) U.S. Cl.
CPC . *A61M 5/31576* (2013.01); *A61M 2005/2414* (2013.01); *A61M 2005/2496* (2013.01); *A61M 2005/31588* (2013.01); *A61M 2205/8206* (2013.01); *A61M 2205/8212* (2013.01)

(56) References Cited

U.S. PATENT DOCUMENTS

| | | | |
|---|---|---|---|
| 8,414,563 B2 | 4/2013 | Kamen et al. | |
| 9,302,089 B2 | 4/2016 | Besko | |
| 9,452,255 B2 | 9/2016 | Tieck et al. | |
| 9,526,826 B2 | 12/2016 | Nagar et al. | |
| 9,682,199 B2 | 6/2017 | Walsh et al. | |
| 9,931,461 B2 | 4/2018 | Kamen et al. | |
| 9,987,416 B2 | 6/2018 | McNall, III et al. | |
| 10,137,243 B2 | 11/2018 | Wang et al. | |
| 10,155,085 B2 | 12/2018 | Gescheit et al. | |
| 10,463,847 B2 | 11/2019 | Shaked et al. | |
| 10,639,417 B2 | 5/2020 | Roberts | |
| 10,688,243 B2 | 6/2020 | Cabiri | |
| 2002/0072733 A1* | 6/2002 | Flaherty | G16H 20/17 604/890.1 |
| 2005/0075608 A1 | 4/2005 | Holdgate et al. | |
| 2008/0269689 A1* | 10/2008 | Edwards | A61M 5/2053 703/11 |
| 2012/0071819 A1* | 3/2012 | Bruggemann | A61M 5/20 604/67 |
| 2014/0074041 A1 | 3/2014 | Pedersen et al. | |
| 2014/0188073 A1* | 7/2014 | Cabiri | A61M 5/14244 604/506 |
| 2016/0366946 A1* | 12/2016 | Murison | H02J 7/0045 |
| 2017/0043092 A1* | 2/2017 | Murakami | A61M 5/20 |
| 2018/0152281 A1 | 5/2018 | Zigelboim et al. | |
| 2018/0154081 A1* | 6/2018 | Bar-El | A61M 5/14244 |
| 2019/0046720 A1 | 2/2019 | Kamen et al. | |
| 2020/0054823 A1 | 2/2020 | Baier et al. | |
| 2020/0085695 A1 | 3/2020 | O'Keefe et al. | |
| 2020/0121909 A1 | 4/2020 | Shaked et al. | |
| 2020/0222623 A1 | 7/2020 | Roberts | |
| 2020/0238012 A1 | 7/2020 | Bar-El et al. | |

FOREIGN PATENT DOCUMENTS

| | | |
|---|---|---|
| EP | 2285360 B1 | 4/2016 |
| EP | 3501584 B1 | 9/2020 |
| JP | 2011-519712 A | 7/2011 |
| JP | 2014-516701 A | 7/2014 |
| JP | 2016-518879 A | 6/2016 |
| WO | 2009088956 A2 | 7/2009 |
| WO | 2012032411 A2 | 3/2012 |
| WO | 2018131046 A1 | 7/2018 |

OTHER PUBLICATIONS

Int'l Preliminary Report of Patentability dated Feb. 11, 2020 in Int'l Application No. PCT/US2018/045506.
Office Action dated Jun. 16, 2021 in Chinese Office Action 201880065173.8.

* cited by examiner

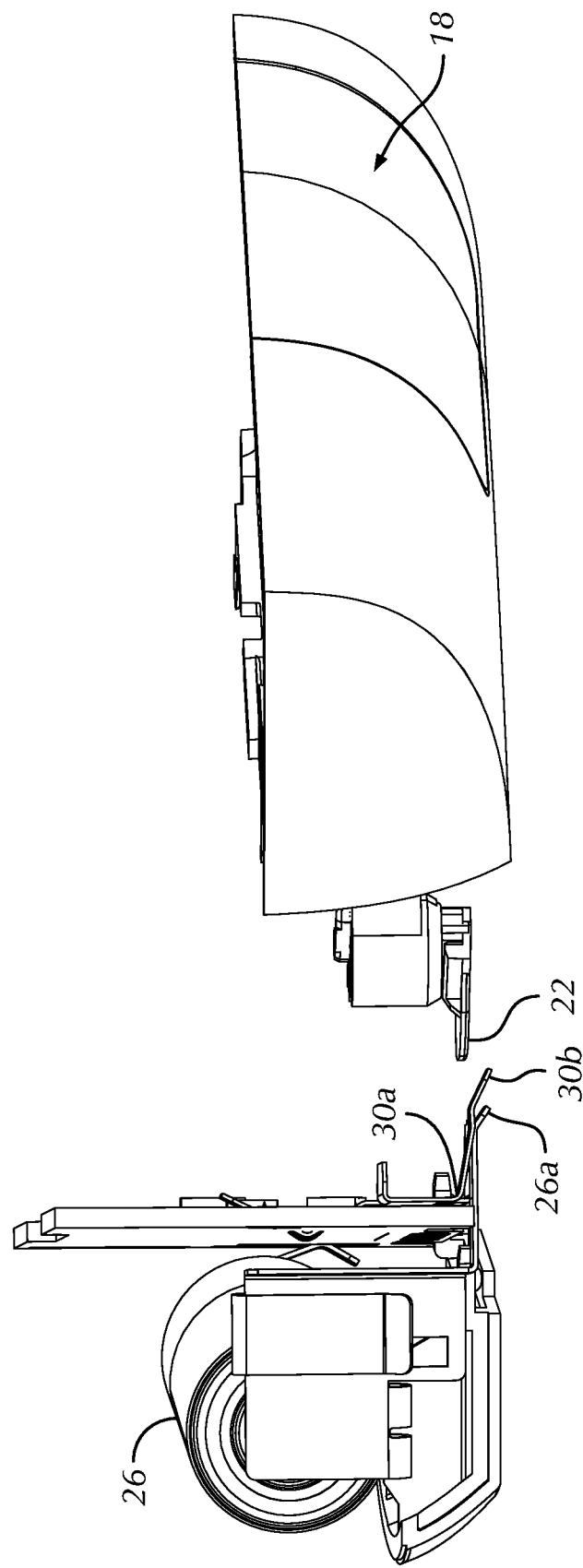

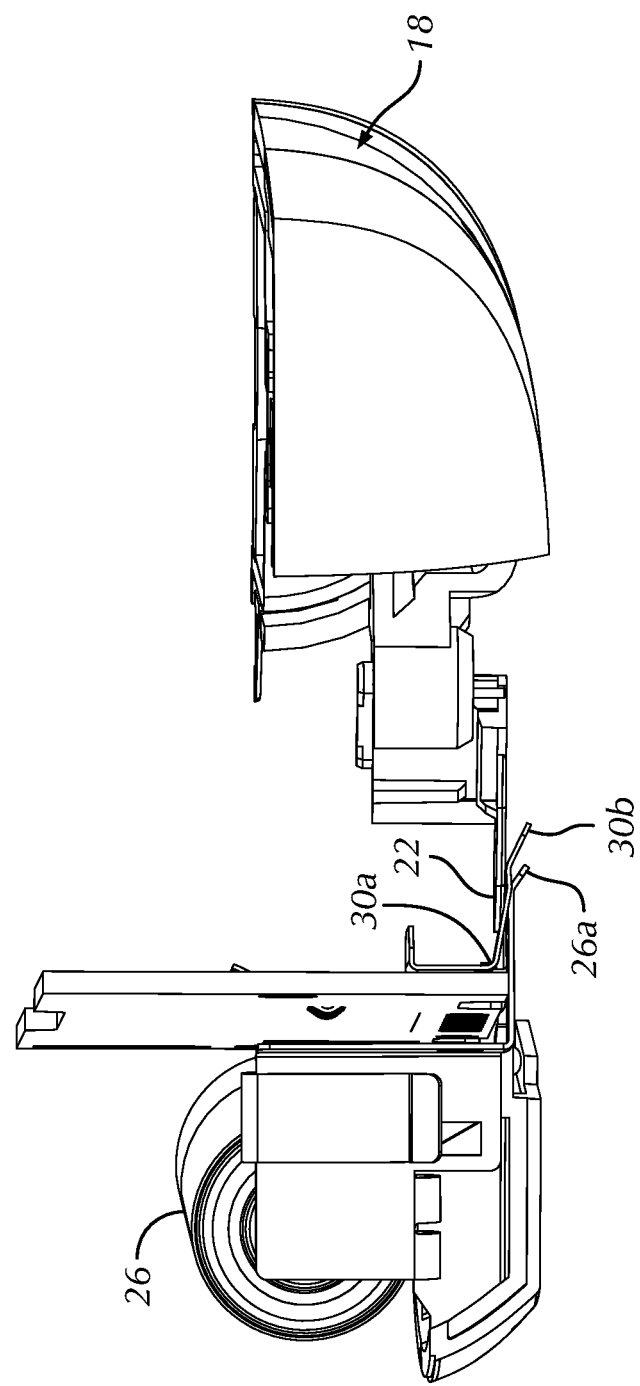

INJECTOR POWER-UP MECHANISM

CROSS-REFERENCE TO RELATED APPLICATIONS

This application is a section 371 of International Application No. PCT/US2018/045506, filed Aug. 7, 2018, which was published on Feb. 14, 2019 under International Publication No. WO 2019/032512 A1, and which claims priority from U.S. Provisional Patent Application No. 62/543,641, titled "Device Power Up Response to Opening Cartridge Bay", filed on Aug. 10, 2017, the entire contents of which are incorporated by reference herein.

BACKGROUND OF THE DISCLOSURE

The present disclosure is generally directed to a cartridge loaded injector, and, more particularly, to a cartridge loaded injector configured to electrically disconnect a power supply of the injector until a user is ready to use the injector.

An injector, such as, for example, a drug injector, is typically loaded with a cartridge containing therein a substance, e.g., a medicament or drug, to be dispensed. Typically, an injector includes an onboard power supply supplying power to power-operated components of the injector. In instances where the injector is not delivered and used by a user for a long period of time after the injector is assembled, the power supply may be at risk of discharging prior to using the injector. Conventional injectors, therefore, electrically disconnect the power supply via a directly removable pull tab which must be removed by the user prior to use to power on the injector.

One drawback of a user removable pull tab is that it must be pulled separately by the user. Finding and pulling the pull tab is not always intuitive and may result in user error. Moreover, utilizing a separately removable pull tab introduces an additional step that must be performed by a user to activate and use the injector.

Therefore, it would be advantageous to manufacture an injector electrically disconnecting the power source until a user intends to use the injector while reducing the number of user performed steps required to prepare the injector for use.

BRIEF SUMMARY OF THE DISCLOSURE

Briefly stated, one aspect of the present disclosure is directed to an injector configured to receive therein a cartridge containing a substance to be dispensed. The injector includes an injector housing and a cartridge door movably mounted to the injector housing. The cartridge door has an open end and an interior channel to receive the cartridge therein through the open end. The cartridge door is movable between a fully closed position, wherein the open end is obscured by the injector housing to prevent insertion of the cartridge into the interior channel, and a fully open position, wherein the open end is sufficiently exposed to receive the cartridge therethrough and into the interior channel. A power supply is employed to power at least one power-operated component of the injector. A power supply circuit electrically connects the power supply with the at least one power-operated component. An electrically insulated arm is movable from a first state, whereat the electrically insulated arm is interposed between a contact of the power supply and an opposing contact of the power supply circuit, to a second state, whereat the electrically insulated arm is removed from between the contact of the power supply and the opposing contact of the power supply circuit, thereby connecting the power supply with the power supply circuit and providing power to the at least one power-operated component. The electrically insulated arm is coupled to the cartridge door and initially positioned in the first state thereof in the fully closed position of the cartridge door, whereby movement of the cartridge door out of the fully closed position toward the fully open position moves the electrically insulated arm to the second state thereof.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings:

FIG. 3A is a perspective view of select components of the injector of FIG. 3, showing the cartridge door in the fully open position thereof and the electrically insulated member in the second state thereof;

FIG. 5A is a perspective view of select components of the injector of FIG. 5, showing the cartridge door in the fully closed position thereof and the electrically insulated member in the second state thereof.

DETAILED DESCRIPTION OF THE DISCLOSURE

Figure 1:
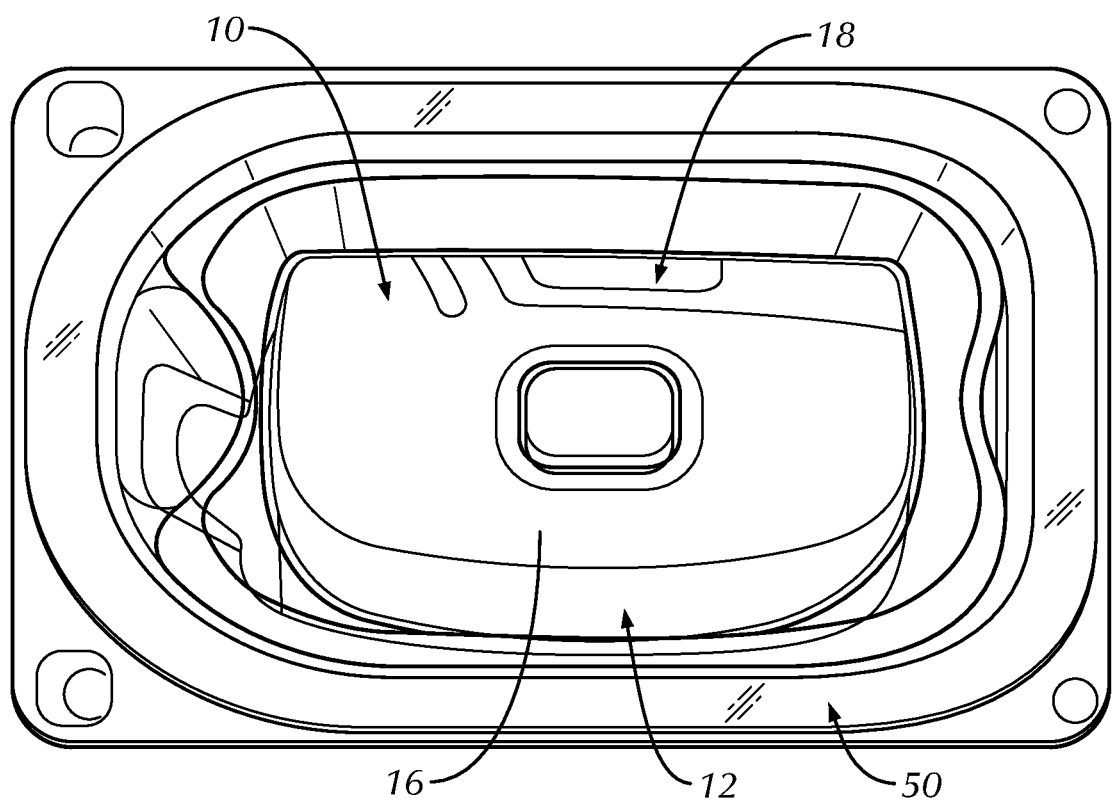
FIG. 1 is a top perspective view of a wearable injector placed in a packaging thereof, in accordance with an embodiment of the present disclosure.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-6 an injector, generally designated 10, in accordance with an embodiment of the present disclosure. In the illustrated embodiment, the injector 10 takes the form of a wearable injector (patch injector), such as, for example, without limitation, a wearable drug injector, but the disclosure is not so limited. The injector 10 may be deliverable to a user in packaging 50 (FIG. 1), as will be discussed in further detail below.

As should be understood by those of ordinary skill in the art, the injector 10 generally includes a housing 12 having a first surface 14 (shown best in FIG. 4) configured to contact a skin surface of a user (not shown), e.g., a patient, the first surface 14 having an opening 14a therein. In the illustrated embodiment, the first surface 14 defines a base surface of the injector housing 12, but the disclosure is not so limited. The housing 12 also includes a second surface 16 (FIG. 1) opposing the first surface 14. In the illustrated embodiment, the second surface 16 defines a top, external surface of the injector housing 12, but the disclosure is not so limited. As also should be understood by those of ordinary skill in the art, an injection needle 15 is movably mounted within the injector housing 12 and is translatable between a retracted position (FIG. 4), wherein at least a tip of the injection needle 15 is contained within the injector housing 12, and an injection position (not shown), wherein at least the tip of the injection needle 15 protrudes from the injector housing 12 through the opening 14a and into the skin of a user (not shown).

The injector 10 is configured to receive therein a sealed cartridge 60 (FIG. 5) containing a substance (not shown), e.g., medicament. The cartridge 60 is sealed at one end by a piston 60a and at another end by a pierceable septum 60b. After (or during) insertion of the cartridge 60 into the injector 10, the cartridge 60 is unsealed and fluidly connected to the injection needle 15, in a manner well understood by those of ordinary skill in the art (via piercing of the septum 60b), to dispense the substance within the cartridge 60 through the injection needle 15 to a user. An injector door 18 is movably mounted to the injector housing 12 between a fully closed position (FIGS. 1-2A) and a fully open position (FIGS. 3, 3A). The injector door 18 is openable to receive the cartridge 60 within the injector 10. In the illustrated embodiment, the injector door 18 takes the form of a cartridge door, but the disclosure is not so limited. The cartridge door 18 includes an open end 18a for receiving, e.g., slidably, the cartridge 60 therethrough, and an interior channel 18b to receive the cartridge 60 therein. The interior channel 18b may be sized and shaped to receive and stabilize the cartridge 60 therein. Alternatively, the interior channel 18b may include a cartridge cradle, a cartridge track, individual stabilizing members, combinations thereof, or the like (not shown) to receive and stabilize the cartridge 60 in the interior channel 18b.

In an at least partially closed position of the cartridge door 18 (FIG. 4), the interior channel 18b is not sufficiently accessible from outside of the injector housing 12 to insert a cartridge 60 therein. For example, in the illustrated embodiment, the open end 18a of the cartridge door 18 is sufficiently obscured/covered by a portion of the injector housing 12 such that access to the interior channel 18b is prevented and the cartridge 60, therefore, cannot be inserted into the interior channel 18b. In the fully open position of the cartridge door 18 (FIG. 3), the open end 18a of the cartridge door 18 is sufficiently exposed/uncovered to permit insertion of the cartridge 60 therethrough and into the interior channel 18b.

In the illustrated embodiment, the cartridge door 18 is pivotably attached to the injector housing 12, e.g., via pin connection 20, proximate a closed, distal end of the interior channel 18b, opposite the open end 18a, but the disclosure is not so limited. As shown best in FIGS. 1 and 2, the cartridge door 18 is substantially flush with the exterior body of the injector housing 12 in the fully closed position. As shown in FIG. 3, the cartridge door 18 is pivoted away from the injector housing 12 in the open position, whereby the interior channel 18b is accessible from the open end 18a of the cartridge door 18. Other non-limiting examples of a cartridge door 18 movably mounted to an injector housing 12 are described in U.S. Patent Application Publication No. 2018/0152281, entitled, "Cartridge Insertion For Drug Delivery Device," the entire contents of which are incorporated by reference herein.

A biasing member 32 may be mounted in the injector housing 12 and configured to bias the cartridge door 18 toward the fully open position thereof. In the illustrated embodiment, the biasing member 32 takes the form of a torsion spring mounted between a non-movable member of the injector housing 12 and a member of the movable cartridge door 18, i.e., the torsion spring 32 abuts the injector housing 12 at one end thereof and abuts the cartridge door 18 at an opposing end thereof. In the closed position of the cartridge door 18, the torsion spring 32 is at least partially compressed, storing potential energy proportional to the amount of twisting thereof. When the torsion spring 32 is uninhibited (as will be described in further detail below), the torsion spring 32 expands, i.e., untwists, to move the cartridge door 18 toward the fully open position thereof. In the illustrated embodiment, the helical center of the torsion spring 32 is mounted around the pin connection 20, but may be otherwise positioned. As also should be understood by those of ordinary skill in the art, the biasing member 32 may alternatively take the form of other members capable of storing and releasing energy. Non-limiting examples include other springs (e.g., coil or leaf springs) and the like. Alternatively, a biasing member 32 may not be employed in the injector 10 and the cartridge door 18 may be manually movable between the fully closed position and the fully open position thereof.

In some embodiments, the injector 10 further includes an elastically deflectable, cantilevered arm 34. The cantilevered arm 34 extends from a fixed end 34a, attached to the injector housing 12, to a flanged, terminal, free end 34b. In some embodiments, the cantilevered arm 34 may be integrally formed, i.e., unitary and monolithic, with the injector housing 12. Alternatively, the cantilevered arm 34 may be separately formed and secured to the injector housing 12.

The cartridge door 18 includes a window 18c in the sidewall thereof, aligned with the cantilevered arm 34.

Figure 2:
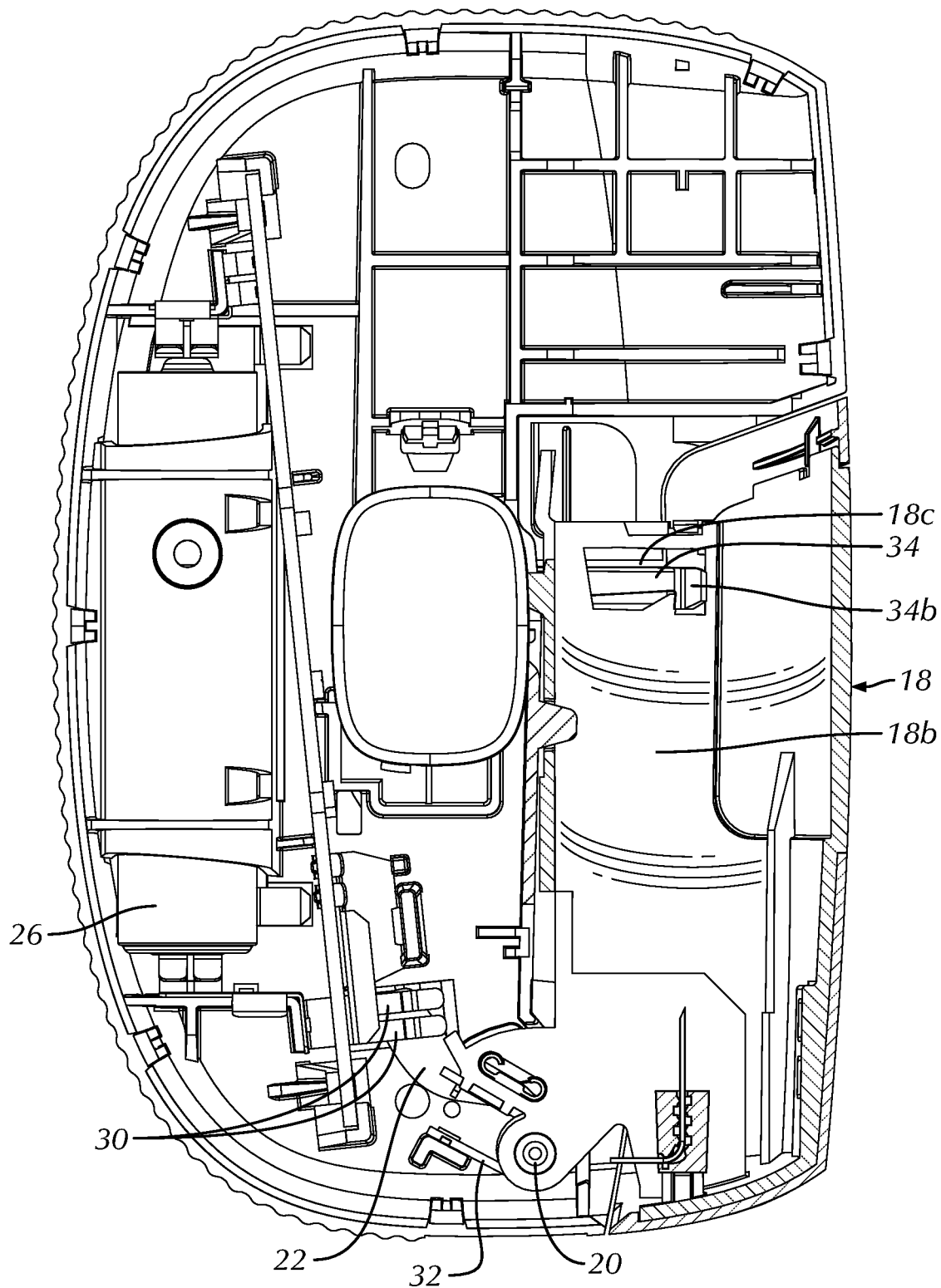
FIG. 2 is a top plan view of the injector of FIG. 1 having a top surface of the injector removed, with an empty cartridge door in an initial fully closed position thereof and an electrically insulated member of the injector in a first state thereof.
Figure 3:
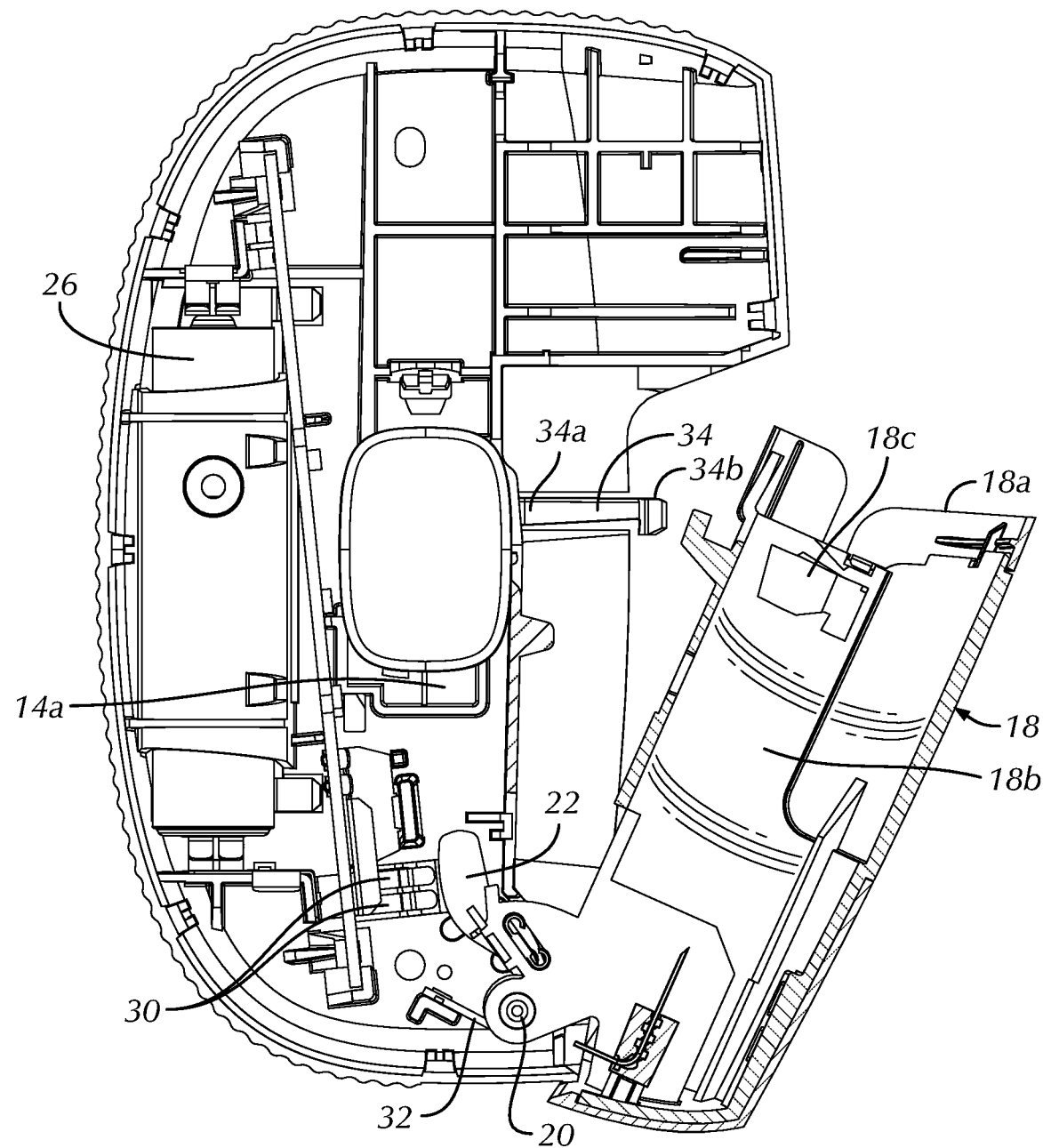
FIG. 3 is a top plan view of the injector of FIG. 1 having the top surface of the injector removed, with an empty cartridge door in a fully open position thereof and the electrically insulated member of the injector in a second state thereof.
Figure 4:
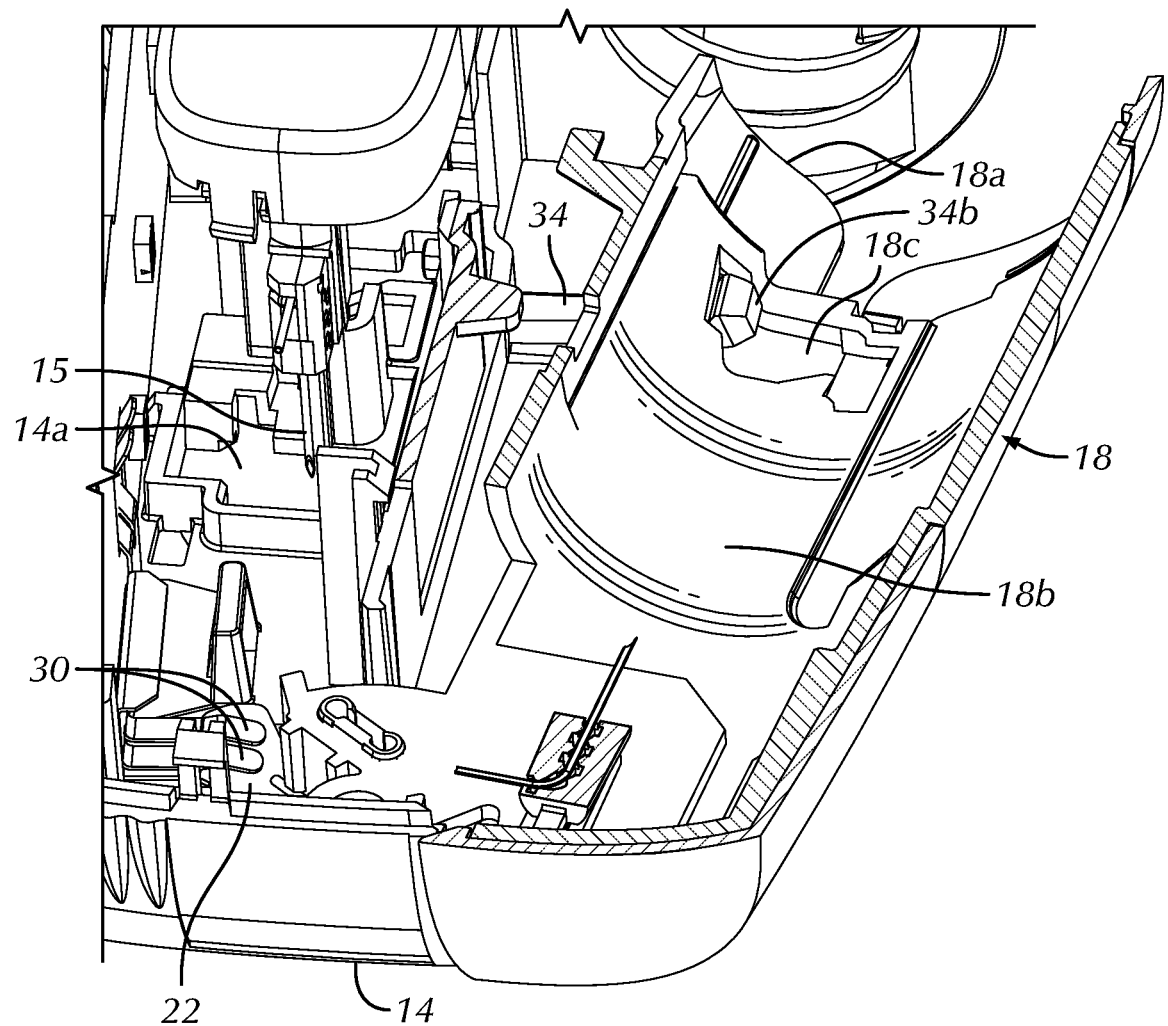
FIG. 4 is a partial perspective view of the injector of FIG. 1 having the top surface of the injector removed, with the cartridge door in a partially closed/partially open position.

In the closed position of the cartridge door 18, when the interior channel 18b has not yet been loaded with a cartridge 60, the cantilevered arm 34 extends into the interior channel 18b of the cartridge door 18 through the window 18c (FIG. 2). In this blocking position of the cantilevered arm 34, the cartridge door 18 is blocked from reaching the fully open position thereof solely under the force of the biasing member 32. That is, the biasing member 32 biases the empty cartridge door 18 from the fully closed position (FIG. 2), wherein the arm 34 projects into the interior channel 18b, toward the fully open position, until the flanged terminal end 34b of the cantilevered arm 34 catches onto the window 18c (FIG. 4), blocking further movement of the cartridge door 18 toward the fully open position thereof solely under the biasing force of the biasing member 32. In the blocking position of the cantilevered arm 34, the cartridge door only reaches a partially open/partially closed position under the bias of the biasing member 32 (FIG. 4). The cantilevered arm 34, however, is deflectable from the blocking position thereof, out of engagement with the window 18c, i.e., unlatching the flanged terminal end 34b from the window 18c (FIG. 3), upon application of a force toward the fully open position of the cartridge door 18 in addition to the biasing force of the biasing member 32, thereby enabling the cartridge door 18 to reach the fully open position thereof. For example, a user may manually pull the cartridge door 18 toward the fully open position thereof, to deflect the arm 34 out of engagement with the window 18c.

As should be understood by those of ordinary skill in the art, the injector 10 further comprises a controller 24 (shown schematically in FIG. 6), e.g., a processor, that directs operation of the injector 10 and a power supply 26 to power the controller 24 and other power-operated components of the injector 10. In the illustrated embodiment, the power supply 26 takes the form of a battery, but the disclosure is not so limited. A power supply circuit 28 (shown schematically in FIG. 6) electrically connects the battery 26 with the controller 24 and the other power-operated components of the injector 10. For example, the power supply circuit 28 may also connect the battery 26 with a driving assembly (not shown) of the injector 10, configured to drive the piston 60a through the cartridge 60 to expel the substance therefrom.

As shown, an electrically insulated member 22 is initially positioned in a first state thereof (FIGS. 2, 2A, 4, and schematically in FIG. 6), whereat the electrically insulated member 22 is interposed between at least one contact 26a (positive or negative) of the power supply 26 and a respective at least one opposing contact 28a of the power supply circuit 28 (of opposite charge from the power supply contact 26a), thereby electrically disconnecting the power supply 26 from the power supply circuit 28 (such that no power is provided to the controller 24 and other injector components) to prevent drainage of the power supply 26 prior to use of the injector 10. The electrically insulated member 22 is movable to a second state (FIGS. 3, 3A, 5), whereat the electrically insulated member 22 is removed from between the at least one contact 26a of the power supply 26 and the respective at least one opposing contact 28a of the power supply circuit 28, thereby electrically connecting the power supply 26 with the power supply circuit 28 and providing power to the injector components, including the controller 24.

In the illustrated embodiment, as shown in FIGS. 2A-5, the electrically insulated member 22 takes the form of polymeric arm mechanically coupled to the cartridge door 18. As should be understood however, the electrically insulated member 22 may be constructed of alternative electrically insulating materials currently known or that later become known. The electrically insulated arm 22 may be fixedly coupled with the cartridge door 18 in a manner well understood by those of ordinary skill in the art. That is, the arm 22 moves, e.g., pivots, along with movement, e.g., pivoting, of the cartridge door 18. Alternatively, the arm 22 may be integrally formed, i.e., unitary and monolithic, with the cartridge door 18.

Figure 2A:
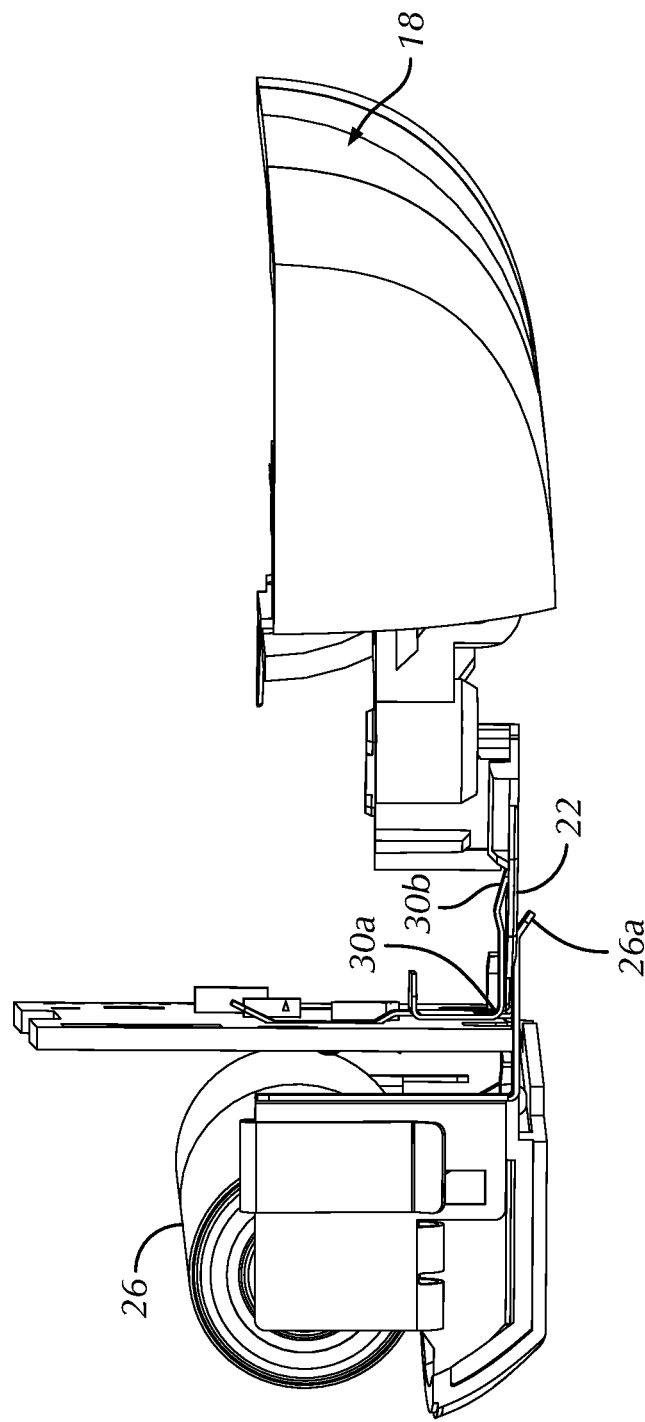
FIG. 2A is a perspective view of select components of the injector of FIG. 2, showing the cartridge door in the fully closed position thereof and the electrically insulated member in the first state thereof.

The arm 22 is configured, i.e., shaped, dimensioned, angled, or a combination thereof, to be initially positioned in the first state thereof in the initial fully closed position of the cartridge door 18 (FIGS. 2, 2A). The arm 22 is also configured to move to the second state thereof (FIGS. 3, 3A) the first time the cartridge door 18 moves out of the fully closed position thereof toward the fully open position thereof. As will be described in further detail below, upon movement of the electrically insulated arm 22 from the initial first state thereof to the second state thereof, the electrically insulated arm 22 remains in the second state thereof, i.e., does not re-disconnect the power supply 26 from the power supply circuit 28, irrespective of subsequent movement of the cartridge door 18. In the illustrated embodiment, as shown in FIG. 3, the arm 22 is configured to reach the second state thereof the first time the cartridge door 18 reaches the fully open position thereof. As should be understood, however, the arm 22 may be configured to reach the second state thereof prior to the cartridge door 18 reaching the fully open position, e.g., upon the cartridge door 18 reaching a partially open position thereof.

In one configuration, the contact 28a of the power supply circuit 28 includes at least one elastically deflectable finger 30 (two deflectable fingers 30 in the illustrated embodiment but the disclosure is not so limited). The fingers 30 are oriented to have a natural, i.e., undeflected, position in which the fingers 30 contact the opposing contact 26a of the power supply 26 (see FIG. 3A). As should be understood by those of ordinary skill in the art, however, the contact 26a of the power supply 26 may alternatively include the at least one elastically deflectable finger oriented to have a natural position in which the finger(s) 30 contacts the opposing contact 28a of the power supply circuit 28. As shown best in FIG. 2A (relative to FIGS. 3A, 5A), the fingers 30 are elastically deflected away from the natural position thereof by the arm 22 interposed between the fingers 30 and the contact 26a in the first state thereof. As the deflection is elastic, the fingers 30 return to the natural position thereof, contacting the opposing contact 26a, when the electrically insulated arm 22 moves to the second state thereof and no longer occupies space between the opposing contacts 26a, 28a. As should be understood by those of ordinary skill in the art, the elastic deflection properties of the finger(s) 30 may be achieved via material properties, dimensions, a combination thereof, or the like. In one embodiment, the finger(s) 30 may be constructed of an elastically deflectable metal.

Figure 5:
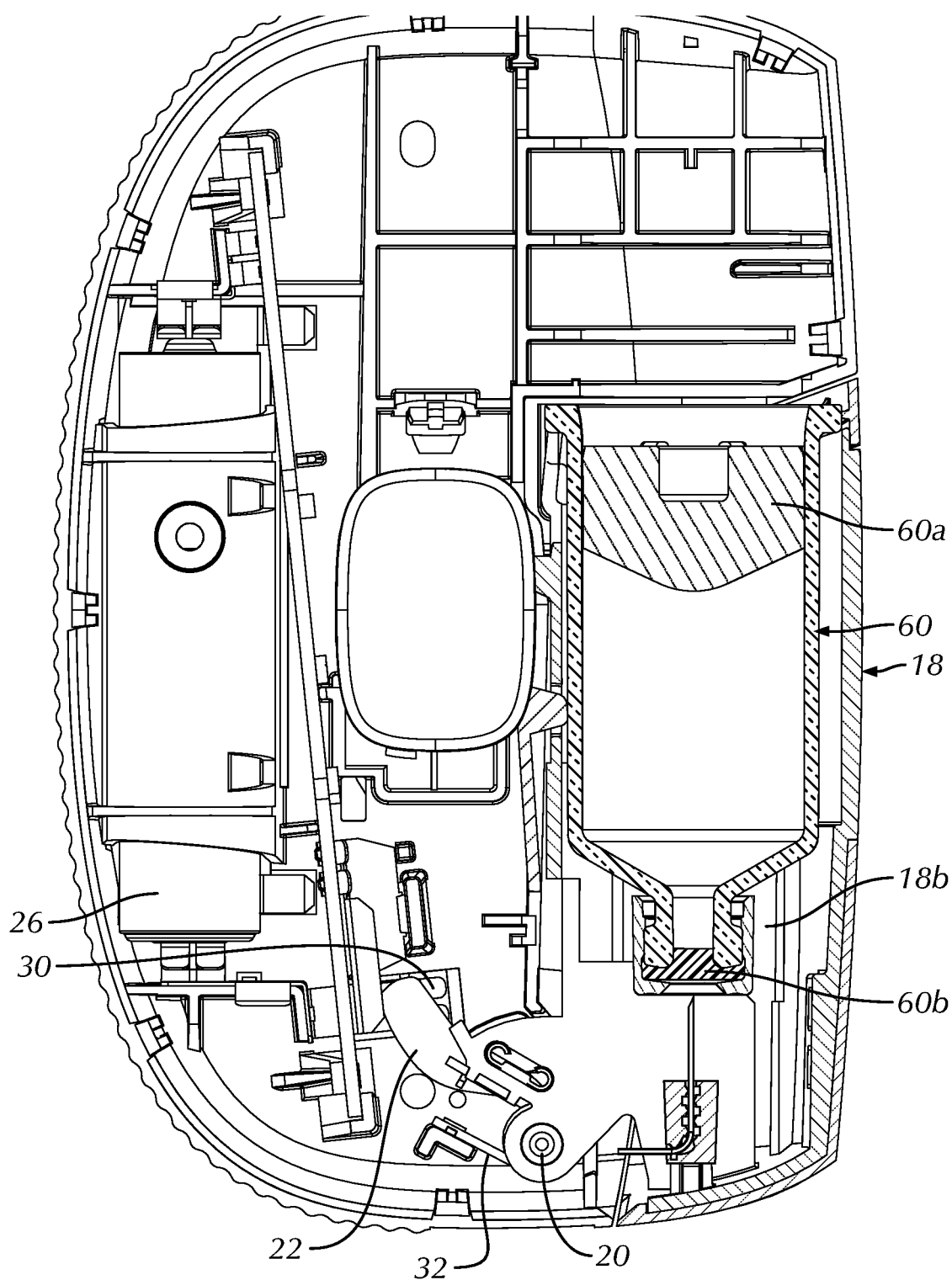
FIG. 5 is a top plan view of the injector of FIG. 1 having the top surface of the injector removed, with the cartridge door loaded with a cartridge therein and returned to the fully closed position thereof, and the electrically insulated member of the injector remaining in the second state thereof.
Figure 6:
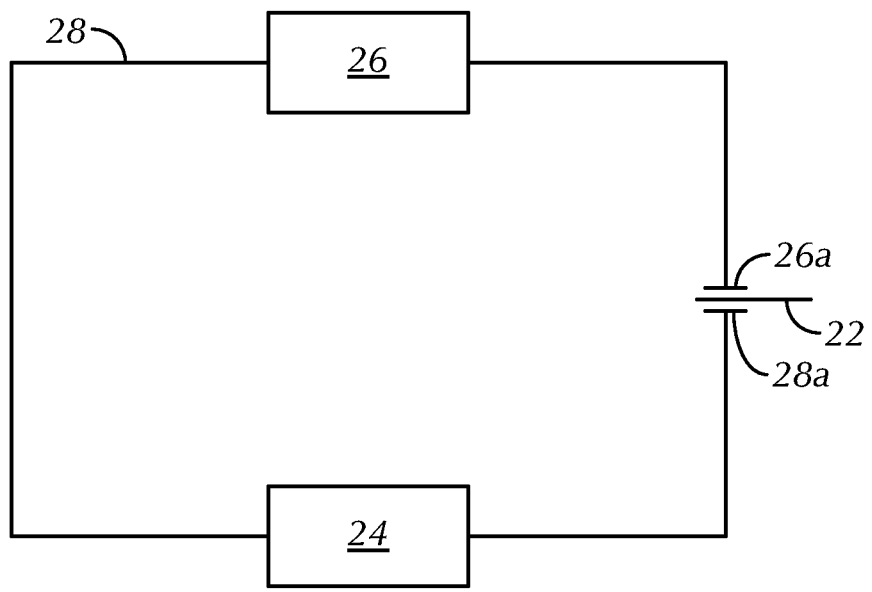
FIG. 6 is a schematic illustration of a power supply circuit of the injector of FIG. 1, having an electrically insulated member interposed between at least one contact of a power supply and a respective at least one opposing contact of the power supply circuit.

As shown best in FIGS. 2A, 3A, and 5A, the finger(s) 30 cantilever from an attached end 30a to an opposing terminal free end 30b. The terminal free end 30b defines an incline extending from the terminal free end 30b in a direction toward the attached end 30a and away from the opposing contact 26a. Accordingly, after the arm 22 moves out of the first state thereof (FIGS. 2, 2A) to the second state thereof (FIGS. 3, 3A) during movement of the cartridge door 18 from the fully closed position thereof to the fully open position thereof, the fingers 30 move from their deflected position to their natural position and contact the opposing contact 26a. Subsequent movement of the cartridge door 18 back toward the fully closed position thereof, i.e., from the second state of the arm 22 in a direction toward the first state thereof, slides the arm 22 up and along the inclined terminal ends 30b of the fingers 30 (which are positioned in their undeflected, natural position), atop the fingers 30 and away from being re-interposed between the fingers 30 and the opposing contact 26a (FIGS. 5, 5A).

In use, the injector 10 may be initially delivered to a user with the cartridge door 18 in the fully closed position thereof, with the electrically insulated arm 22 in the first state thereof. Alternatively, the injector 10 may be delivered to a user with the cartridge door 18 in a sufficiently closed position, wherein the electrically insulated arm 22 is in the first state thereof. Initial positioning of the electrically insulated arm 22 in the first state thereof prevents drainage of the power supply 26 prior to use of the injector, e.g., during delivery and/or storage. Where a biasing member 32 is employed to bias the cartridge door 18 into the open position, the injector packaging 50 may maintain the cartridge door 18 in the fully closed position thereof (FIG. 1), against the force of the biasing member 32. As should be understood, however, the cartridge door 18 may be positioned in the fully closed position thereof via other mechanisms currently known or that later become known. As one example, a removable liner (not shown) may be positioned over a portion of the cartridge door 18 and the injector housing 12 to maintain the door 18 in the closed position. Alternatively, the cartridge door 18 may be locked, e.g., in the fully closed position (with or without the presence of the biasing member 32).

Where the cartridge door 18 is biased to the open position thereof, e.g., via the biasing member 32, removal of the injector 10 from the packaging 50 thereof enables the biasing member 32 to move the cartridge door 18 out of the fully closed position thereof toward the open position thereof. Where a cantilevered arm 34 is employed in the injector 10, the arm 34 will block the cartridge door 18 from reaching the fully open position thereof (as previously explained), and maintain the cartridge door 18 in a partially closed/partially open position (FIG. 4). In the partially closed/partially open position, as shown in FIG. 4, the electrically insulated arm 22 remains in the first state thereof, i.e., has not sufficiently moved to a position not interposed between the contacts 26a, 28a. In the partially closed/partially open position, the cartridge 60 is not yet insertable into the interior channel 18b. Accordingly, when a user is ready to use the injector 10, the user pulls the cartridge door 18, deflecting the cantilevered arm 34 out of the blocking position thereof, and moves the cartridge door 18 to the fully open position thereof (FIG. 3). Alternatively, where the cartridge door 18 is not biased to the open position thereof, a user may manually move the cartridge door 18 from the fully closed position thereof to the fully open position thereof. For example, without limitation, if the injector 10 is initially delivered to a user with the cartridge door 18 in the fully closed position thereof, a pull tab (not shown) attached to the cartridge door 18 may be employed, so that a user may pull the cartridge door 18 open via the pull tab. The pull tab may be single use and disconnect from the cartridge door 18 after moving the door 18 from the initial fully closed position to the initial fully open position thereof. Alternatively, the injector 10 may be delivered to a user with the cartridge door 18 partially opened such that a user may grasp a protruding portion of the door 18 to fully open the cartridge door 18 when ready for use.

In the fully open position of the cartridge door 18, the electrically insulated arm 22 is moved into the second state thereof, thereby electrically connecting the power supply 26 with the power supply circuit 28 and providing power to the injector components, including the controller 24. The injector 10 turns on once power is provided to the controller 24. Optionally, when the controller 24 is powered on, the controller 24 may be configured to conduct an initial self-test on operability of at least one component of the injector 10 to determine whether the injector 10 is properly functioning and ready for use and/or to inform the user when the cartridge 60 may be inserted into the cartridge door 18. For example, an audible tone and/or visual indicator, a combination thereof or the like, indicative of injector 10 readiness or injector 10 malfunction, respectively, may be activated.

Advantageously, the electrically insulated member 22 is permanently mounted within the injector housing 12, i.e., the member 22 is not removable from the injector 10 without disassembly of the injector 10. The electrically insulated member 22 is also not visible or directly accessible by a user. The electrically insulated arm 22 is, therefore, only movable into the second state thereof when the user is ready to use the injector 10 and purposefully moves the cartridge door 18 to the fully open position thereof. Accordingly, the power supply 26 is preserved until the user is ready to use the injector 10, and the risk of premature power supply drainage is reduced. Further advantageously, the steps required to be performed by a user to activate and prepare the injector 10 for use are reduced. That is, a user both opens the cartridge door 18 to insert a cartridge 60 therein and powers on the injector 10 in one step. Decreasing the number of actions required by a user to activate and prepare the injector 10 for use simplifies the injector 10 for the user and reduces the potential for user error.

In the fully open position of the cartridge door 18, the cartridge 60 may be inserted into the interior channel 18b, and, thereafter, the cartridge door 18 may be moved back into the fully closed position thereof (FIG. 5). As previously explained, the electrically insulated member 22 remains in the second state thereof despite movement of the cartridge door 18 back to the fully closed position thereof, and, thus, the power supply 26 remains electrically connected with the power supply circuit 28, thereby continuing to provide power to the power-operated injector components. After loading the cartridge 60 and closing the door 18, the controller 24 may then direct the driving assembly to drive the piston 60a through the cartridge 60 to expel the substance from the cartridge 60 and out of the injector 10 through the injection needle 15, in a manner well understood by those of ordinary skill in the art.

It will be appreciated by those skilled in the art that changes could be made to the embodiments described above without departing from the broad inventive concept thereof. As one example, the electrically insulated member 22 may be connected to the pull tab. As another example, the electrically insulated member 22 may take the form of a mechanical switch of the power supply circuit 28. It is understood, therefore, that this invention is not limited to the particular embodiments disclosed, but it is intended to cover modifications within the spirit and scope of the present invention, as set forth in the appended claims.

We claim:

1. An injector configured to receive therein a cartridge containing a substance to be dispensed, the injector comprising:
   an injector housing;

a cartridge door movably mounted to the injector housing and having an open end and an interior channel to receive the cartridge therein through the open end, the cartridge door being movable between a fully closed position, wherein the open end is obscured by the injector housing to prevent insertion of the cartridge into the interior channel, and a fully open position, wherein the open end is sufficiently exposed to receive the cartridge therethrough and into the interior channel;

a power supply configured to power at least one power-operated component of the injector;

a power supply circuit electrically connecting the power supply with the at least one power-operated component; and an electrically insulated arm movable from a first state, whereat the electrically insulated arm is interposed between a contact of the power supply and an opposing contact of the power supply circuit, to a second state, whereat the electrically insulated arm is removed from between the contact of the power supply and the opposing contact of the power supply circuit, thereby connecting the power supply with the power supply circuit and providing power to the at least one power-operated component, wherein the electrically insulated arm is coupled to the cartridge door and initially positioned in the first state thereof in the fully closed position of the cartridge door, whereby movement of the cartridge door out of the fully closed position toward the fully open position moves the electrically insulated arm to the second state thereof, and wherein upon movement of the electrically insulated arm from the initial first state to the second state, the electrically insulated arm remains in the second state thereof irrespective of subsequent movement of the cartridge door.

2. The injector of claim 1, wherein at least one of the contact of the power supply or the opposing contact of the power supply circuit comprises a deflectable finger, the finger having a natural position in which the finger contacts the opposing contact, wherein the finger is deflected away from the natural position thereof in the first state of the electrically insulated arm and the finger returns to the natural position thereof when the electrically insulated arm moves to the second state thereof.

3. The injector of claim 2, wherein the finger comprises a terminal free end, the terminal free end defining an incline extending from the terminal free end in a direction away from the opposing contact, whereby movement of the electrically insulated arm from the second state thereof in a direction toward the first state thereof slides the electrically insulated arm along the incline and away from being re-interposed between the finger and the opposing contact.

4. The injector of claim 1, wherein the electrically insulated arm reaches the second state thereof in the fully open position of the cartridge door.

5. The injector of claim 1, wherein the cartridge door is pivotably mounted to the injector housing, the electrically insulated arm being pivotable with the cartridge door from the first state to the second state thereof.

6. The injector of claim 1, further comprising a biasing member configured to apply a biasing force upon the cartridge door, thereby biasing the cartridge door toward the fully open position thereof.

7. The injector of claim 6, further comprising an arm positioned in a blocking position blocking the cartridge door from reaching the fully open position thereof under the bias forcing of the biasing member, the arm being deflectable from the blocking position upon application of a force in addition to the biasing force, thereby enabling the cartridge door to reach the fully open position thereof.

8. The injector of claim 7, wherein the cartridge door includes a window in a sidewall thereof, the arm being positioned to catch onto the window in the blocking position and the arm being deflectable out of engagement with the window upon application of the force in addition to the biasing force to enable the cartridge door to reach the fully open position thereof.

9. The injector of claim 6, in combination with an injector packaging, the packaging being configured to maintain the cartridge door in the fully closed position thereof, against the biasing force of the biasing member, when the injector is positioned in the packaging.

10. The injector of claim 9, wherein upon removal of the injector from the packaging, the cartridge door is moved towards the fully open position by the biasing member and the electrically insulated arm is moved to the second state.

11. An injector configured to receive therein a cartridge containing a substance to be dispensed, the injector comprising:

an injector housing;

a cartridge door movably mounted to the injector housing and having an open end and an interior channel to receive the cartridge therein through the open end, the cartridge door being movable between a fully closed position, wherein the open end is obscured by the injector housing to prevent insertion of the cartridge into the interior channel, and a fully open position, wherein the open end is sufficiently exposed to receive the cartridge therethrough and into the interior channel;

a power supply configured to power at least one power-operated component of the injector;

a power supply circuit electrically connecting the power supply with the at least one power-operated component; and an electrically insulated arm permanently mounted within the injector housing and movable from a first state, whereat the electrically insulated arm is interposed between a contact of the power supply and an opposing contact of the power supply circuit, to a second state, whereat the electrically insulated arm is removed from between the contact of the power supply and the opposing contact of the power supply circuit, thereby connecting the power supply with the power supply circuit and providing power to the at least one power-operated component, wherein the electrically insulated arm is coupled to the cartridge door and initially positioned in the first state thereof in the fully closed position of the cartridge door, whereby movement of the cartridge door out of the fully closed position toward the fully open position moves the electrically insulated arm to the second state thereof.

12. The injector of claim 11, wherein at least one of the contact of the power supply or the opposing contact of the power supply circuit comprises a deflectable finger, the finger having a natural position in which the finger contacts the opposing contact, wherein the finger is deflected away from the natural position thereof in the first state of the electrically insulated arm and the finger returns to the natural position thereof when the electrically insulated arm moves to the second state thereof.

13. The injector of claim 12, wherein the finger comprises a terminal free end, the terminal free end defining an incline extending from the terminal free end in a direction away from the opposing contact, whereby movement of the electrically insulated arm from the second state thereof in a direction toward the first state thereof slides the electrically insulated arm along the incline and away from being re-interposed between the finger and the opposing contact.

14. The injector of claim 11, wherein the electrically insulated arm reaches the second state thereof in the fully open position of the cartridge door.

15. The injector of claim 11, wherein the cartridge door is pivotably mounted to the injector housing, the electrically insulated arm being pivotable with the cartridge door from the first state to the second state thereof.

16. The injector of claim 11, further comprising a biasing member configured to apply a biasing force upon the cartridge door, thereby biasing the cartridge door toward the fully open position thereof.

17. The injector of claim 16, further comprising an arm positioned in a blocking position blocking the cartridge door from reaching the fully open position thereof under the bias forcing of the biasing member, the arm being deflectable from the blocking position upon application of a force in addition to the biasing force, thereby enabling the cartridge door to reach the fully open position thereof.

18. The injector of claim 17, wherein the cartridge door includes a window in a sidewall thereof, the arm being positioned to catch onto the window in the blocking position and the arm being deflectable out of engagement with the window upon application of the force in addition to the biasing force to enable the cartridge door to reach the fully open position thereof.

19. The injector of claim 16, in combination with an injector packaging, the packaging being configured to maintain the cartridge door in the fully closed position thereof, against the biasing force of the biasing member, when the injector is positioned in the packaging.

20. The injector of claim 19, wherein upon removal of the injector from the packaging, the cartridge door is moved towards the fully open position by the biasing member and the electrically insulated arm is moved to the second state.

* * * * *